(12) United States Patent
Obagi et al.

(10) Patent No.: US 9,248,160 B1
(45) Date of Patent: Feb. 2, 2016

(54) POST-PROCEDURE SKIN CARE SYSTEMS, COMPOSITIONS, AND METHODS OF USE THEREOF

(71) Applicant: ZO SKIN HEALTH, INC., Irvine, CA (US)

(72) Inventors: Zein E. Obagi, Irvine, CA (US); Frederick W. Woodin, Jr., Irvine, CA (US)

(73) Assignee: ZO SKIN HEALTH, INC., Irvine, CA (US)

( * ) Notice: Subject to any disclaimer, the term of this patent is extended or adjusted under 35 U.S.C. 154(b) by 0 days.

(21) Appl. No.: 14/811,264

(22) Filed: Jul. 28, 2015

(51) Int. Cl.
| | |
|---|---|
| *A61K 33/06* | (2006.01) |
| *A61K 47/36* | (2006.01) |
| *A61K 31/722* | (2006.01) |
| *A61L 15/44* | (2006.01) |
| *A61L 15/18* | (2006.01) |
| *A61L 15/20* | (2006.01) |
| *A61K 38/16* | (2006.01) |
| *A61K 31/19* | (2006.01) |
| *A61K 45/06* | (2006.01) |
| *A61L 15/32* | (2006.01) |
| *A61L 15/28* | (2006.01) |

(52) U.S. Cl.
CPC ............... *A61K 38/168* (2013.01); *A61K 31/19* (2013.01); *A61K 31/722* (2013.01); *A61K 33/06* (2013.01); *A61K 45/06* (2013.01); *A61K 47/36* (2013.01); *A61L 15/18* (2013.01); *A61L 15/20* (2013.01); *A61L 15/28* (2013.01); *A61L 15/32* (2013.01); *A61L 15/44* (2013.01); *A61L 2300/102* (2013.01); *A61L 2300/21* (2013.01); *A61L 2300/232* (2013.01); *A61L 2300/252* (2013.01)

(58) Field of Classification Search
None
See application file for complete search history.

(56) References Cited

U.S. PATENT DOCUMENTS

| | | | |
|---|---|---|---|
| 4,572,906 A | 2/1986 | Sparkes et al. | |
| 5,773,033 A | 6/1998 | Cochrum et al. | |
| 5,902,798 A | 5/1999 | Gouda et al. | |
| 9,144,434 B1 | 9/2015 | Rodan et al. | |
| 2009/0068255 A1* | 3/2009 | Yu ....................... | A61K 8/0212 424/450 |

FOREIGN PATENT DOCUMENTS

| | | |
|---|---|---|
| WO | 2011/004399 A2 | 1/2011 |
| WO | 2013/044111 A1 | 3/2013 |

OTHER PUBLICATIONS

Domeboro, "Domeboro® Astringent Solution Product Info," <http://www.domeboro.com/about-domeboro/>, published Nov. 11, 2014, p. 1-3.*
"AQUALANCE Technical Brochure", SEDERMA Company, 42 pages, (2008).
"AVONLAC 182 GLC", Whey Protein, Whey Peptide and Flaxseed Technologies, Glanbia Nutritionals, Inc., 1 page, (2012).
"ChitoClear—A Natural Polymer Solution for Cosmetics", Sandream Enterprises LLC, 1 page, (2015).
"Clarisoy Soy Protein Isolate", Burcon Nutrascience, 2 pages, (Jan. 2014).
"Botanicals Plus! Discover the Boundless Benefits of Botanical Blends", Botanicals Plus, 54 pages, (2007).
"SymPeptide: Novel Peptides: Anti-Aging, Anti-Acne", Symrise, 23 pages, (2012).
"Product Information: TECH-O #11-080 (Avena Sativa (Oat) Kernel Protein USP/NF)", Beacon CMP Corporation, 1 page, (publication data unknown).
"Product Information", Beacon CMP Corporation, 8 pages, (publication data unknown).
"TEGO Pep 4-17: New bioactive tetrapeptide with superior collagen boosting activity", Evonik Industries, 5 pages, (2008).

* cited by examiner

*Primary Examiner* — Tracy Vivlemore
*Assistant Examiner* — Monica Shin
(74) *Attorney, Agent, or Firm* — Vorys, Sater, Seymour and Pease LLP

(57) ABSTRACT

Provided are topical biocompatible compositions including a topical wound healing composition, a topical soothing composition and epidermal/dermal wound healing/repair composition. Also provided are methods of using the biocompatible compositions for treating and/or preventing comprimised, and methods for producing the biocompatible compositions.

23 Claims, 4 Drawing Sheets

Subject pre-procedure

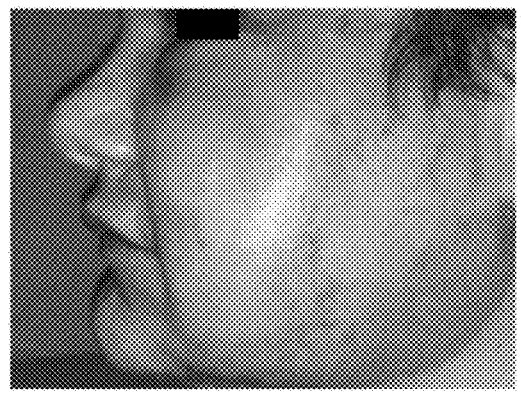
Subject Post Recovery Side
2 days post-procedure
Comparative Post Recovery Side
2 days post-procedure
FIG. 2A
FIG. 2B Subject Post Recovery Side
5 days post-procedure Comparative Post Recovery Side
5 days post-procedure Subject Post Recovery Side
9 days post-procedure Comparative Post Recovery Side
9 days post-procedure

POST-PROCEDURE SKIN CARE SYSTEMS, COMPOSITIONS, AND METHODS OF USE THEREOF

FIELD

The present subject matter relates to post-procedure skin care systems and kits including the same, topical compositions for treating compromised skin, and methods of use thereof.

BACKGROUND

Skin resurfacing is used to remove the various layers of the epidermis and/or dermis to promote healthier skin by, for example, regenerating collagen, elastin, and epidermis. In addition skin resurfacing can rejuvenate the facial skin, and improve the appearance of fine line and wrinkles. Skin resurfacing can also remove superficial blemishes such as the brown spots of ageing, dilated capillaries, and small keratoses.

One procedure currently in wide use for skin resurfacing involves exposure to a laser, including for example, ablative and/or nonablative laser technology. Because any given laser emits light of only one wavelength (or color), they work in cosmetic applications through a process called selective photothermolysis. To be effective, the wavelength of the light beam must be in sync with the color of the target which is to be addressed, whether that be brown spots, unsightly red broken capillaries or some other undesirable skin condition. The most-commonly used lasers for the treatment of pigmented lesions, such as sun spots, age spots melasma and other forms of hyperpigmentation are the pulsed dye, Nd:YAG and fractional (Fraxel) lasers, along with nonlaser, light-based treatments, such as IPL.

Lasers useful in cosmetic procedures also include $CO_2$ (carbon dioxide) laser or Erbium YAG for treating lines and wrinkles, the removal of warts and skin tags, acne scars and for cutting skin in laser-assisted surgery. Pulsed Dye Lasers have also shown some success, along with less aggressive nonlaser, light-based treatments, such as intense pulsed light (IPL) and LED photofacials. Most cosmetic laser procedures provide some level of superficial tightening because they produce a controlled injury of the skin, which encourages increased collagen production. For more significant tightening results $CO_2$ lasers or nonlaser, light-based treatments, such as Titan infrared devices and Thermage radio-frequency based systems may be used.

Resurfacing methods also include chemical peeling and dermabrasion. A chemical peel causes a chemical burn. Dermabrasion mechanically removes the epidermis and a variable layer of dermis. Recently, a rapid scanning device has been added to the cutting laser, enabling a predictable depth of skin to be destroyed. Resurfacing methods treat superficial wrinkles and repair skin aged by light.

Skin resurfacing procedures result in predictable post-operative sequelae including facial edema, wound exudates, erythema, pain, pruritis, hyperpigmentation, milia formation, and acne.

SUMMARY

The present subject matter relates to biocompatible topical compositions, kits including the same and methods of accelerating the wound healing of post-procedure or otherwise compromised skin. More specifically, provided is a topical wound healing composition, a topical soothing composition and an epidermal/dermal repair composition. The topical wound healing composition described herein, for example, utilizes a unique, unanticipated combination system of food grade, high potency protein constituents, a hemostatic agent and antifungal agents for enhanced skin tissue repair.

The presently described topical wound healing composition can comprise or consist of one or more astringents. The topical wound healing compositions may also comprise one or more protein, a protein complex, and/or chitosan. The topical wound healing composition may also include a filler or carrier. The presently described topical wound healing composition may further include a pH adjusting agent, a coloring agent and/or a non-formaldehyde releasing preservative.

The presently described topical wound healing compositions can be free from one or more of the following: gluten; vitamin D; a growth hormone; a paraben; an EU 26 fragrance allergen; and a formaldehyde releasing preservative.

Also provided is a topical soothing composition. The topical soothing composition may comprise or consist of one or more of a glycosaminoglycan (GAG) stimulator, an anti-inflammatory, an antioxidant, and a DNA repair component.

The GAG stimulator, which repairs compromised skin, may be any substance that stimulates glycosaminoglycan. For example, the GAG stimulator may be disodium acetyl glucosamine phosphate (DAGP).

Anti-inflammatory or anti-irritant components used in the topical soothing composition may include, for example, one or more of: Brassica Oleracea (Broccoli) Extract; Helianthus Annuus (Sunflower) Seed Oil; Avena Sativa (Oat) Kernel Flour Protein; and/or Beta-Glucan.

The one or more antioxidants used in the topical soothing composition may include, for example, one or more antioxidant including, for example, Ubiquinone (Co-Enzyme Q10); Tocopheryl Acetate; Ascorbic Acid; and Retinyl Palmitate. The antioxidant component may include an antioxidant complex, that is formulated as a 12-hour time release encapsulate. The antioxidant complex may comprise or consist of Polymethyl Methacrylate and one or more Tocopheryl Acetate, Ascorbic Acid and Retinyl Palmitate, or other suitable antioxidant.

The topical soothing formulation may include of a DNA repair component. The DNA repair component may comprise or consist of one or more of Adenosine Triphosphate, Hydrolyzed Vegetable Protein, Proline, Acetyl Tyrosine, or the like.

The topical soothing composition may also comprise or consist of one or more absorption promoters, anti-bacterial agents, anti-microbial agents, anti-fungal agents, emollients, self-emulsifying elastomer gels, emulsifiers, solvents, surfactants, preservatives, skin protectants, moisturizers, anti-Inflammatory agents, humectants and/or fragrances.

In addition, provided is an epidermal/dermal wound healing/repair composition. The epidermal/dermal wound healing/repair composition may comprise or consist of one or more of one or more of a skin protectant to protect and relieves dryness and itching due to irritation or otherwise compromised skin. As used herein, the epidermal/dermal wound healing/repair may be reffered to as, an epidermal/dermal wound healing composition, an epidermal wound healing/repair composition, an epidermal/dermal wound repair composition, or the like. Peptides may be included in the epidermal/dermal wound healing/repair. The repair composition may also include a moisturizer. One or more anti-inflammatory agent may also be included in the epidermal repair composition to calm redness and sooth irritated or otherwise compromised skin.

The epidermal/dermal wound healing/repair composition may include one or more antioxidants or an antioxidant complex. The antioxidant complex may be formulated as a 12-hour time release encapsulate.

Optionally, the epidermal repair composition may also include one or more of a carrier, a solvent, a thickening agent, a humectant, an emulsifier, anti-bacterial agents, anti-microbial agents, anti-fungal agents, an emollient, an emulsifiying agent, a skin protectant active, a neutralizing agent, a preservative, a collagen Stimulator, a DNA protector, a moisturizing agent, soy phospholipids, a DNA repairing agent and a skin conditioning agent.

Also provided is a post-procedure skin kit. The post-procedure skin kit may comprise or consist of one or more of topical wound healing composition, a topical soothing composition and an epidermal/dermal wound healing/repair composition. The kit may further include instructions for use, packaging as well as additional compositions for treating post-procedure or otherwise compromised skin.

The presently described subject matter also relates to a method of reducing skin irritation in a subject, comprising or consisting of topically administering to the subject a therapeutically effective amount of one or more biocompatible topical composition described herein.

The presently described subject matter further relates to a method for treating compromised skin in a subject, comprising topically administering to the subject in need thereof a therapeutically effective amount of one or more of the presently described biocompatible topical composition.

The presently described subject matter also relates to a method for treating post-procedure skin in a subject, comprising topically administering to a subject in need thereof a therapeutically effective amount of one or more a biocompatible topical composition described herein.

BRIEF DESCRIPTION OF THE FIGURES

FIG. 2A shows the right side profile view of patient two (2) days post chemical peel after instructed use of the present post-procedure biocompatible topical compositions;

FIG. 2B shows the left side view of the same patient on the same day after instructed use of a comparative post procedure topical regime.

DETAILED DESCRIPTION

Definitions

Figure 1:
FIG. 1 shows a frontal view of a patient pre-procedure.

The term "about" as used herein refers to a quantity, level, value, dimension, size, or amount that varies to some extent based on the context in which it is used. For example, such variation can be by as much as 5%. At the least, each numerical parameter can be construed in light of the number of reported significant digits and by applying ordinary rounding techniques.

As used herein, the terms "administer," "administering," and "administration," refer to any method which, in sound medical practice, delivers the composition to a subject in such a manner as to provide a therapeutic effect.

For the purposes of the presently described subject matter, the present topical biocompatible compositions can be topically administered. For example, administration can include, but is not limited to, direct topical administration. For example, a viscous formulation, including for example a cream, gel, ointment, or salve formulation, or a liquid formulation, for example, a solution, can be administered directly to a desired skin surface. Administration can also be accomplished via a compress or a wet dressing. For example, a liquid, e.g., solution, emulsion, suspension, etc., formulation of the presently described topical composition can be applied to a skin surface via a compress or wet dressing.

The term "antibacterial agent," as used herein refers to a substance that kills bacteria or inhibits their growth. Non-limiting examples of suitable antibacterial agents include chlorphenesin and potassium sorbate.

The term "antifungal agent," as used herein refers to a substance that kills fungi or inhibits their growth. Suitable antifungal agents include one or more of chlorphenesin, Potassium sorbate 5-fluorocytosine, Abafungin, Acrisorcin, Amorolfme, Albaconazole, Albendazole, Amorolfme, Amphotericin B, Anidulafungin, Arasertaconazole, Azithromycin, Becliconazole, Benzodithiazole, Bifonazole, Butenafine, Butoconazole, Calbistrin, Caspofungin, Chloroxine, Chlorphenesin, Ciclopiroxolamine, Ciclopirox, Cioteronel, Clotrimazole, Croconazole, Cytoporins, Deoxymulundocandin, Eberconazole, Econazole, Efungumab, Fenticonazole, Flavanoid glycosides, Fluconazole, Flutrimazole, Flucytosine, Fosfluconazole, Genaconazole, Gentian violet, Griseofulvin, Griseofulvin-PEG, Haloprogin, Hydroxy itraconazole, Isoconazole, Itraconazole, Ketoconazole, Lanoconazole, Letrazuril, Liranaftate, Luliconazole, Micafungin, Miconazole, Mycophenolic acid, Naftifine, N-chlorotaurine, Natamycin, Nitazoxanide, Nitro- ethylene based antifungals, Nystatin, Omoconazole, Oxiconazole, Polyene macrolide, Posaconazole, Pramiconazole, Quinolone analogs, Rapamycin, Ravuconazole, Rilopirox, Samidazole, Sertaconazole, Sitamaquine, Sordaricin, Squalestatin, Squalene, a Squaline Expoxidase Inhibitor, Sulconazole, Sultriecin, Tafenoquine, Terbinafine, Terconazole, Tioconazole, Tolnaftate, and Voriconazole, sodium propionate, sodium formate, propionic acid, and formic acid.

The term "antimicrobial agent," as used herein refers to a substance that kills microorganisms or inhibits their growth. Antimicrobial agents can include antibacterial agents that act against bacteria and antifungal agents that act against fungi. Antimicrobial agents can further include antiviral agents.

As used herein, the term "anti-inflammatory agent," refers to any substance, for example, a chemical compound, that acts to reduce one or more indications of inflammation, such indications including, but not limited to, swelling, redness, tenderness, and pain. Such compounds can include but are not limited to Beta Glucan, Avena Sativa (Oat) Kernel Meal, Avena Sativa (Oat) Kernal Protein USP, Avena sativa (Oat) Kernal Flour, whey protein concentrates, and combinations thereof.

The term "Avena sativa," refers to oats. The term "Avena sativa kernel" refers to the hull-less kernel of oats. Avena sativa can include any form of oat, including colloidal oatmeal, oat extract, oat kernel, and oat protein. Oats are naturally gluten free. Colloidal oatmeal is classified as a skin protectant by the FDA and is oats ground into a fine powder. Oats contain beta-glucans; proteins including avenalin and avenin where the hull-less oat kernel contains up to 24% of such protein; alkaloids; fats; minerals; saponins; a sterol flavonoid; and vitamin B. Avena sativa can contain avenanthramides. Colloidal oatmeal can contain starches, beta-glucan, and oat phenols that can absorb ultraviolet light. Avena sativa, suitable for use in the presently described topical compositions can include but is not limited to one or more of the following: Avena sativa kernel, Avena sativa kernel protein and colloidal oatmeal.

"Absorption promoter" refers to one or more combinations of fatty acids suitable for use in the present topical biocompatible compositions. Non-limiting examples of absorption promoters include one or more of caprylic/capric triglycerides (Migyol 810 and 812), caprylic/capric/linoleic triglycerides (Miglyol 818), caprylic/capric/myristic/stearic fatty acid triglycerides (Softisan 378), capylic/capric/succinic fatty acid triglycerides (Miglyol 829), caprylic/capric triglycerides with stearalkonium 10luminium and propylene carbonate (Migyol Gel T), caprylic/capric triglycerides with stearalkonium hectorite and propylene carbonate (Migyol Gel B)

The term "antioxidant" refers to an atom or molecule that has a greater oxidation potential than a second atom or molecule, such that the antioxidant is preferentially oxidized instead of the second atom or molecule. For example, an antioxidant can have a greater oxidation potential than hematein, and thus help prevent oxidation of hematein to oxyhematein. Furthermore, an antioxidant also can function as a reducing agent, for example, a reducing agent that converts oxyhematein back to hematein. Antioxidants can be present in the disclosed compositions at concentrations ranging from about 1 mM to about 1M, for example, from about 5 mM to about 500 mM, such as from about 50 mM to about 150 mM.

Non-limiting examples of antioxidants include Tocopheryl Acetate, Ascorbic Acid and/or Retinyl Palmitate, soluble soy protein, Idebenone, coenzyme Q10, Lycopene, Epigallocatechin 3-gallate (EGCG), green tea polyphenols (GTP), Silymarin, CoffeeBerry® (VDF FutureCeuticals: antioxidant extracted from the fruit of the coffee plant Coffea 10lumini), Grape seed extract, Pomegranate extracts, Genistein, pycnogenol, niacinamide, methionine, glutathione, tocotrienol, dimethyl glycine, betaine, butylated hydroxyanisole, butylated hydroxytoluene, turmerin, vitamin E, ascorbyl palmitate, deteroxime mesylate, methyl paraben, ethyl paraben, butylated hydroxyanisole, butylated hydroxytoluene, propyl gallate, sodium or potassium metabisulfite, sodium or potassium 10luminiu, alpha tocopherol or derivatives thereof, sodium ascorbate, disodium edentate, BHA (butylated hydroxyanisole), flavonoids, a pharmaceutically acceptable salt or ester of the mentioned compounds, and mixtures thereof. Flavonoids include, for example, quercetin, morin, naringenin and hesperetin, taxifolin, afzelin, quercitrin, myricitrin, genistein, apigenin and biochanin A, flavone, flavopiridol, isoflavonoids such as the soy isoflavonoid, genistein, catechins such as the tea catechin epigallocatechin gallate, flavonol, epicatechin, hesperetin, chrysin, diosmin, hesperidin, luteolin, and rutin.

The phrase "anti-oxidant complex" refers to a delayed, extended or time release formulation comprising polymethacrylate and one or more anti-oxidant. The anti-oxidant complex may be a 12 hour extended release formulation.

The terms "astringent" or "astringent component," as used herein refers to any substance that when applied to the skin or mucous membranes cause a local and limited protein coagulant effect. An astringent substance shrinks or constricts body tissues, and is therefore used as a skin protectant. Suitable astringents can include any biocompatible over the counter (OTC) astringent, including for example, but not limited to, a combination of 11luminium sulfate tetradecahydrate and calcium acetate monohydrate which together can react to form the astringent 11luminium acetate. Other suitable astringent substances can include but are not limited to, 11luminium sulfate and witch hazel.

The term "biocompatible" or "physiologically compatible," as used herein, refers to the ability to be in contact with a living system without producing a significant adverse effect, for example, by not being toxic, injurious, or physiologically reactive.

As used herein, the term "chitosan," refers to a linear polysaccharide composed of randomly distributed β-(1-4)-linked D-glucosamine (deacetylated unit) and N-acetyl-D-glucosamine (acetylated unit). Also included within the meaning of Chitosan herein are salts and derivatives thereof, including, e.g., chitosan quaternized derivatives. Chitosan is water soluble a biopolymer. The term "chitosan salt" refers to a salt of chitosan, including for example, but not limited to, one or more salts of succinic acid, lactic acid, ascorbic acid, and hydrochloric acid. Chitosan is also commonly known as poliglusam, deacetylchitin, and poly-(D)glucosamine. The degree of deacetylation can be from 60% to 100%, from 70% to 90%, from 90% to 95%, from 90% to 100%, from 95% to 100%, or from 98% to 100%, including for example 90%, 95%, and 98% or 100% (sold as ORISTAR™ Chitosan) deacetylation.

As described herein, Chitosan has the following chemical formula:

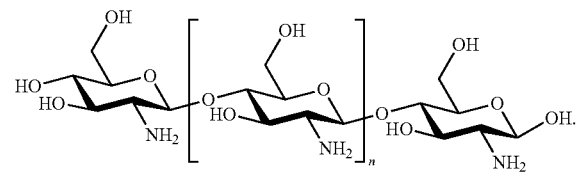

As used herein, the phrases an "effective amount" or a "therapeutically effective amount" of a composition and/or active agent or ingredient, which are synonymous herein, refer to an amount of the active agent sufficient enough to have a therapeutic effect upon administration. A therapeutically effective amount of the active agent may, will, or is expected to cause a relief of symptoms. Effective amounts of the active agent will vary with the particular condition or conditions being treated, the severity of the condition, the duration of the treatment, the specific components of the composition being used, and like factors. For example, the presently described compositions can be topically applied in an amount sufficient to cover an affected area. The presently described compositions can be topically applied in an amount sufficient to cover an affected area plus a margin of healthy skin or tissue surrounding the affected area, for example, a margin of about 0.5 inches.

As used herein the term "emollient" refers to any product applied to the skin which soothes irritation of the skin, including, for example, ointments, liniments, lotions, creams, moisturisers, oils, skin softeners, soaps, shampoo, sunscreens, cosmetics and the like. Non-limiting examples of emollients suitable for the biocompatible topical compositions herein include, for example, Hydrogenated Polyisobutene, C-12-C-15 alcohols benzoate, isopropyl myristate, mineral oils, lanolin and lanolin derivatives, and triglycerides such as coconut oil, cetostearyl alcohol, cetyl alcohol, isopropyl palmitate, caprylic/capric triglyceride, PPG-2 myristyl ether propionate, dimethicone, methicone, petrolatum, lanolin, and mineral oil.

As used herein "emulsifier" refers to a compound or substance at acts as a stabilizer for emulsions preventing the liquids from separating. Non-limiting examples of emulsifiers suitable for the present biocompatible topical compositions incude. PEG-15/Lauryl Dimethicone Crosspolymer, Polyglyceryl-4 Isostearate and/or Cetyl PEG/PPG 10/1 Dimethicone and/or Hexyl Laurate, polyoxyethylene fatty ethers derived from stearyl alcohols, Isopropyl Isostearate, Cetyl Alcohol, polyethylene glycol stearate, a glycol stearate, a glyceryl stearate, ceteryl alcohol, ceteareth 20, methylcellulose, cetomacrogol 1000, and lecithin. The terms "filler" and "carrier" mean any inert or non-inert substance added to one or more of the biocompatible topical compositions described herein to increase bulk, weight, viscosity, opacity, or strength. The filler may, for example, be one or more of a complex branched glucan, water, tribehenin, a natural or artificial wax component, talc, mica, silica, kaolin, cellulose powders, dextrin, powdered pregelatinized starch, non-gelling amylopectin starch and glucose polymers laponite, polyamide powders, such as Nylon® powder, poly-β-alanine powder and polyethylene powder, powders of tetrafluoroethylene polymers (Teflon®), lauroyllysine, starch, boron nitride, particles of acrylic polymer, for example, particles of acrylic acid copolymer, and silicone resin microbeads, precipitated calcium carbonate, dicalcium phosphate, magnesium carbonate, magnesium hydrocarbonate, hydroxyapatite. The at least one filler may or may not be surface-treated, for example, to make them lipophilic.

The term "humectant" refers to a substance capable of reducing the loss of moisture. Non-limiting examples of humectants include, for example, glycerin, sodium hyaluronate, glycerin, glycerol, propylene glycol, glyceryl triacetate, a lanolin product, such as PPG-12-PEG 50, polyhydric alcohols, water soluble alkoxylated nonionic polymers, and mixtures thereof. Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sultate, sodium hyaluronate, sodium adenosin phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof. Commercially available humectants herein include: glycerin with tradenames STAR and SUPEROL available from The Procter & Gamble Company, CRODEROL GA7000 available from Croda Universal Ltd., PRECERIN series available from Unichema, and a same tradename as the chemical name available from NOF; propylene glycol with tradename LEXOL PG-865/855 available from Inolex, 1,2-PROPYLENE GLYCOL USP available from BASF; sorbitol with tradenames LIPONIC series available from Lipo, SORBO, ALEX, A-625, and A-641 available from ICI, and UNISWEET 70, UNISWEET CONC available from UPI; dipropylene glycol with the same tradename available from BASF; diglycerin with tradename DIGLYCEROL available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from Ichimaru Pharcos; sodium adenosin phophate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Tomen; and polyethylene glycols with the tradename CARBOWAX series available from Union Carbide.

As used herein, the term "moisturizer" refers to a composition that, when applied to a surface (e.g. skin, mucosal tissue, wound, etc.) causes retention of water within, near or at the surface. Non-limiting examples of suitable moisturizers for the present biocompatible topical compositions include Erythritol and/or Homarine HCI, Sodium Hyaluronate, aloe vera, phospholipids, phospholipid mixtures, sodium hyaluronate, glycerol of urea, hydroxyethyl urea, glycerin, shea butter, myristyl myristate, pentaerythrityl distearate, acetylated glycol stearate, sodium stearoyl glutamate, hydrogenated polyisobutene, hydrogenated lecithin, pentylene glycol, glucose, dimethicone, sodium hyaluronate, VP/VA copolymer, Ceramide III, amodimethicone.

As used herein the terms "pH adjuster" and "neutralizing agent" refer to any composition, compound, or agent, suitable for adjusting the pH of the presently described topical compositions without negatively affecting any property thereof. Suitable pH adjusters can include any acid or base. Suitable pH adjusters can include but are not limited to aminomethyl propanol, hydrochloric acid, sulfuric acid, citric acid, acetic acid, formic acid, phosphoric acid, tartric acid, and triethanolamine.

The term "protein system," "protein components" and "multi-protein complex," which may be used interchangeably herein, refer to one or more cosmetically acceptable soluble protein components. Such protein components can include but are not limited to one or more pharmaceutically acceptable soluble protein components, including for example, cosmetically acceptable soluble protein components. Such protein components can include but are not limited to one or more pharmaceutically acceptable soluble protein components. Such protein components can include milk or whey derived cosmetically acceptable soluble protein components. Suitable cosmetically acceptable soluble protein components may include but are not limited to one or more of Avena sativa kernel protein, soy protein, and whey protein. Suitable cosmetically acceptable soluble protein components may also include one or more of hydrolyzed milk protein, hydrolyzed soy protein, hydrolyzed corn protein, hydrolyzed avacado protein, hydrolyzed sweet almond protein, hydrolyzed barley protein, hydrolyzed hemp seed protein, hydrolyzed brazil nut protein, hydrolyzed sesame protein, hydrolyzed pea protein, hydrolyzed cottonseed protein, and hydrolyzed hazelnut protein.

Suitable and/or miscible protein systems may comprise or consist of soy protein, whey protein, and avena sativa kernel protein. Suitable protein systems may also comprise or consist of soy protein and whey protein.

As used herein, "skin protectant" or refers to any material capable of protecting, treating compromised skin. Non-limiting examples of skin protectants include one or more of Calcium Acetate, Aluminum sulfate, Coenzyme Q 10, petrolatum, Vitamin E acetate, Butylene Glycol and/or Acetyl Tyrosine and/or Proline and/or Hydrogenated Vegetable Protein and/or Adenosine Triphosphate and/or water, Avena Sativa (Oat) Kernel Meal, Avena Sativa (Oat) Kernal Protein USP, Avena sativa (Oat) Kernal Flour, allantoin, aluminum hydroxide gel, bismuth subnitrate, boric acid, calamine, cocoa butter, dimethicone, glycerin, kaolin, live yeast cell derivative, shark liver oil, sodium bicarbonate, sulfur, zinc acetate, zinc carbonate, alpha-hydroxy acids, beta-hydroxy acids, alpha-keto acids, derivatives thereof and mixtures thereof.

As used herein, the term "salt" refers to salts of certain ingredient(s) which possess the same activity as the unmodified compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids.

As used herein the term "preservative" refers to any known biocompatible preservative that functions by inhibiting bacteria and/or fungi, and/or by inhibiting oxidation. Suitable preservatives can include but are not limited to antimicrobial agents and/or antioxidants. Suitable antimicrobial agents can include but are not limited to benzoates, benzyl alcohol, sodium benzoate, n-alkyl dimethyl benzyl ammonium chloride, Chlorphenesin, methylparaben, propylparaben, ethylhexylglycerin, phenoxyethanol, chlorocresol, potassium sorbate, sorbic acid, bronopol, methychloroisothiazolinone, methylisothiazolinone, sorbates, propionates, and nitrites. Suitable antioxidants can include but are not limited to vitamin C, butylated hydroxytoluene (BHT), sulphites, and vitamin E.

As used herein, "peptide" refers to both naturally occurring and synthesized peptides. The peptides may be capable of promoting re-epithelialization, FGF/Collagen Stimulation and Cell Proliferation (e.g., matrix remodeling, tissue repair, wound healing). Suitable peptides include but are not limited to, for example, Myristoyl Pentapeptide-11, Myristoyl Pentapeptide-8, Myristoyl Hexapeptide-4, Myristoyl Octapeptide-1, Tripeptide-1, Acetyl Hexapeptide-8, Acetyl Dipeptide-1, Caproyl Tetrapeptide-3, Carnosine, Glutathione, Marine Oligopeptide, Marine Oligopeptide, Palmitoyl Oligopeptide, Human Oligopeptide-1 (EGF), Acetyl Tetrapeptide-3, Palmitoyl Tetrapeptide-7, Acetyl Tetrapeptide-5, Palmitoyl Hexapeptide-14, Pentapeptide-3, Nonapeptide-1, Acetyl Hexapeptide, Hexapeptide-11, SH-Polypeptide-15, Hexanoyl Dipeptide-3, Acetyl Octapeptide-3, Palmitoyl Tripeptide-5, Palmitoyl Dipeptide-5, Palmitoyl Dipeptide-6, Acetyl Tetrapeptide-2, and Myristoyl Pentapeptide-17, acetyl tetrapeptide-3. Suitable preservatives can include any non-formaldehyde donating preservative, including for example, potassium sorbate.

As used herein, the phrase "formaldehyde releasing preservative," refers to preservatives that release methylene glycol, the alcohol form of formaldehyde, over the shelf life of a product. Formaldehyde releasing preservatives can include but are not limited to dimethyl-dimethyl (DMDM) hydantoin, diazolidinyl urea, imidazolidinyl urea, methenamine, quaternium-15, 2-Bromo-2-nitropropane-1,3-diol, tris(hydroxymethyl) nitromethane, and sodium hydroxymethylglycinate.

As used herein, the term "compromised skin," refers to skin that exhibits impaired skin integrity. Such compromised skin can include compromised facial skin, and skin of the hands, neck, and/or chest. Impaired skin integrity can result from skin damage, a skin procedure, skin irritation, skin inflammation, a burn to the skin (e.g., sunburn), a chronic skin condition arising from a disease or disorder (e.g., rosacea, acne, eczema, shingles, chickenpox, and the like), allergic contact dermatitis (e.g., due to exposure to plants of the genus Rhus which contain urushiol, e.g., poison ivy, poison oak, and poison sumac), atopic dermatitis, or can be a dermatological side effect of a course of treatment.

As used herein the term "skin procedure" refers to any procedure used to treat the skin and can include, but is not limited to, for example, one or more skin rejuvenation procedures. Skin rejuvenation procedures can include skin resurfacing procedures, including for example, chemical peels, laser resurfacing, and dermabrasion or dermaplaning. Laser resurfacing can include ablative laser treatment ($CO_2$ lasers, fractionated $CO_2$ lasers), erbium laser resurfacing, non-ablative laser treatment, or a combination thereof. Other skin procedures can include one or more of non-laser light-based treatment (IPL, infrared treatments), plasma resurfacing treatment (PORTRAIT) and thermal radio-frequency based treatment.

Chemical peels can include, but are not limited to, for example, glycolic acid peels, trichloracetic acid peels, and phenol peels.

Ablative laser resurfacing treatments can include, but are not limited to, fractional $CO_2$ resurfacing, Erbium laser treatments done with an ER:YAG laser, and ablative fractional resurfacing treatments. Both fractional $CO_2$ resurfacing and Erbium laser treatments are both used to treat deep wrinkles, sun damage, and age spots. Fractional laser photothermolysis (FP) provides similar results to that of a $CO_2$ laser but with less risk of scarring and less downtime.

Non-ablative laser treatments can include, but are not limited to, non-ablative fractional resurfacing, and pulsed dye laser treatments.

Non-laser light-based treatments can include, but are not limited to, intense pulsed light (IPL) treatments, Infra Red treatments, and photodynamic therapy. Intense Pulsed Light (IPL) employs a broad spectrum of light, as opposed to a single wavelength emitted by lasers.

As used herein the term "post-procedure reaction" refers to any reaction caused by a skin procedure. Such reactions can include one or more of inflammation, irritation, redness (erythema), swelling, edema, wound exudate, discoloration, skin lightening, hyperpigmentation, scarring, bruising, itching (pruritis), stinging, activation of herpes infections, bacterial infections, blisters, scabbing, milia formation, and acne.

As used herein the term "post-procedure skin" refers to skin that has been subjected to a skin procedure as defined herein.

One or more of the presently described topical compositions can be topically administered to the skin of a patient to treat, one or more of the following: compromised skin; post-procedure skin; skin irritation; skin inflammation; skin damage; burns to the skin; and skin sunburn.

Compromised skin, post-procedure skin, burned skin, and/or damaged skin, can exhibit one or more of skin irritation, skin inflammation, swelling, redness, scabbing, itchiness, and pain.

Skin irritation and/or skin inflammation can also be caused by one or more of: a procedure; an allergic reaction; contact with a skin irritant such as poison ivy, poison oak, poison sumac, an insect bite, soaps, detergents, cosmetics, and/or metals (metal jewelry); an infection; a skin treatment such as acne treatment (e.g., topical or oral retinoids, acetyl salicylic acid, benzyl peroxide, or the like); and trauma.

The phrase "substantially pure" as used herein refers to an individual compound form, which is substantially devoid of all other forms, as well as degradation products of a form, and any residual solvent, and is at least 85% pure on a % weight basis, unless otherwise specified. The compound form can have at least 90% purity on a % weight basis, at least 93% purity on a % weight basis, at least 95% purity on a % weight basis, or at least 97% purity on a % weight basis. As used herein substantially pure may refer to food grade ingredients used in topical compositions.

As used herein, "subject" or "individual" or "animal" or "patient" or "mammal," refers to any subject, particularly a mammalian subject, for whom diagnosis, prognosis, or therapy is desired, for example, a human.

As used herein, a "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. A useful composition herein needs only to reduce the severity of a disease, disorder, or condition, reduce the severity of symptoms associated therewith, provide improvement to a patient or subject's quality of life, or delay or inhibit the onset of a disease, disorder, or condition.

As used herein, the phrase "re-epithelialization," refers to the acceleration of the natural re-epithelialization process and cellular regeneration of skin upon topical use of one or more of the presently described topical biocompatible compositions, such skin including for example, post-procedure skin, damaged skin, burned skin, irritated skin, and/or inflamed skin, at a rate greater than that observed in such skin absent the use of one or more of the presently described topical biocompatible compositions.

The term "whey protein" refers to the soluble protein found in milk whey that has been clotted by rennin, examples of which include alpha-lactalbumin, lactoglobulin, and lactoferrin. The presently described topical composition may comprise whey protein or may be free from whey protein.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application. For example, "an" astringent component refers to both one astringent component or a mixture comprising two or more astringent components.

Unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained.

Throughout the application, descriptions of various embodiments use "comprising" language; however, it will be understood by one of skill in the art, that in some specific instances, an embodiment can alternatively be described using the language "consisting essentially of" or "consisting of."

Other terms as used herein are meant to be defined by their well-known meanings in the art.

Topical Biocompatible Compositions

The presently described topical biocompatible compositions include, for example, a topical healing composition, including, e.g., an astringent solution powder, a topical soothing composition, and an epidermal repair composition.

The presently described topical biocompatible compositions can be provided in any form, including, but not limited to a gel, a cream, a lotion, an ointment, a foam, an aerosol, a powder, a solution, an emulsion, and a serum. p Topical Wound Healing Composition The presently described topical wound healing compositions can be provided in any form. For example, the topical wound healing compositions can be provided in the form of a water soluble, flowable powder that, when mixed with water, forms a solution. The solution, when applied to compromised skin, can calm irritation, reduce inflammation, prevent scabbing, and/or can prevent or ameliorate post-procedure reactions.

The presently described topical wound healing compositions can provide soothing, effective relief of irritation by forming a skin barrier to help protect compromised skin and help minimize increased trans-epidermal water loss from compromised skin, and may hydrate such skin to prevent scabbing and crusting. The topical wound healing composition may be invisible, or substantially invisible, when applied to the skin. Added antimicrobial action can protect compromised skin against infection. Whey protein promotes skin recovery while oat and soy proteins may prevent redness and irritation. Chitosan can prevent scabbing and crusting during the recovery process. Combined these multi-modal biological effects help speed the wound healing process and minimize post-procedural recovery times.

The presently described topical wound healing compositions can comprise or consist of one or more astringents. The one or more astringent may be present in the described topical biocompatible compositions in an amount of, for example, from about 20 wt % to about 95 wt %; from about 40 wt % to about 90 wt %; from about 60 wt % to about 90 wt %; from about 70 wt % to about 85% wt %; from about 75 wt % to about 83 wt %; from about 78 % to about 81 wt %; about 75 wt %, about 76 wt %; about 77 wt %, about 78 wt %, about 79 wt %; about 80 wt %, about 81 wt %, about 82 wt %; about 83 wt %, about 84 wt %, or about 85 wt %.

The topical wound healing compositions may also comprise one or more protein, a protein complex, and/or chitosan. The protein complex may comprise or consist of a protein such as, e.g., Avena Sativa (Oat) Kernal Protein USP, soluble soy protein and/or whey protein.

According to the subject matter herein, the one or more protein may be a food grade protein having specific protein content. The one or more protein may be substantially pure, as defined herein above. For example, the avena sativa kernel may have a specific protein content of about >10% present protein by weight. The soy protein may be an isolated soy food/beverage grade protein with a specific protein content of about >5% (TBC). The whey protein may be a food/beverage grade whey protein with a specific protein content of >80%.

One example of an avena sativa protein that can be utilized in the topical healing composition is a TECH-O® #11-080. The avena sativa protein may have a specific protein content of about content may be more than about 10%, 12.50% or 19.00% by weight of the avena sativa protein. The fat content of the avena sativa protein may be greater than 5.00%, 6.00% or 9.00%. The avena sativa may optionally include ash fat or a carbohydrate in an amount of, for example, about 0.01% or greater.

An example of of a soy protein that may be used in the present compositions is CLARISOY™100. The soy protein may be a micronized soy protein. The soy protein may be a water soluble soy protein that forms a substanitlay transparent solution when disolleved. The soy protein may be 100% solublue.

An example of a whey protein according to the present subject matter is AVONLAC™ 182 GLC. The whey protein may include 80% or more specific protein by weight.

Any protein or protein complex utilized in the topical wound healing composition may also include vitamins, amino acids, moisture, fat, minerals, sugars, or the like. For example, the protein may include vitimans, including but not limite to, for example, Vitamin A, Vitamin $B_1$, Vitamin $B_3$, Vitamin $B_6$, Vitamin $B_7$, Vitamin $B_9$, Vitamin $B_{12}$, Vitamin C, Vitamin D, Vitamin E, Vitamin K. Additionaly, amino acids useful in the present proteins may include, e.g., Glycine, Alanine, Valine, Leucine, Isoleucine, Serine, Cysteine, Selenocysteine, Threonine, Methionine, Proline, Phenylalanine, Tyrosine, Tryptophan, Histidine, Lysine, Arginine, Aspartate, Glutamate, Asparagine and Glutamine.

Each of the one or more proteins and/or the protein complex may be present in the topical wound healing compositions in an amount of, for example, from 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01 % to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt; or in any other amount within any of the above ranges.

Chitosan may be present in the topical wound healing composition in an amount of from >0.01 wt % to about 50 wt %; >0.01 wt % to about 20 wt %; >0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01 % to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 50 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; or in any other amount within any of the above ranges.

The topical wound healing composition may also include a filler or carrier, such as, for example, dextrin. The filler or carrier may be present in the wound healing composition in an amount from 0.01 wt % to about 50 wt %; from 0.01 wt % to about 30 wt %; from 0.01 wt % to about 25 wt %; from 0.01 wt % to about 20 wt %; from 0.01 wt % to about 15 wt %; 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01% to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 30 wt %; from 0.1 wt % to about 25 wt %; from 0.1 wt % to about 20 wt %; from 0.1 wt % to about 15 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about 30 wt %; from 0.5 wt % to about 25 wt %; from 0.5 wt % to about 20 wt %; from 0.5 wt % to about 15 wt %; from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 20 wt %; 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 20; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 30 wt %; from 1 wt % to about 20 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 30 wt %; from about 1.5 wt % to about 20 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 30 wt %; from about 3 wt % to about 20 wt %; from about 3 wt % to about 10 wt ; from about 3 wt % to about 9 wt %; from about 3 wt % to about 8 wt %; from about 3 wt % to about 7 wt %; from about 3 wt % to about 6 wt %; from about 3 wt % to about 5 wt %; from about 3 wt % to about 4.5 wt %; from about 3 wt % to about 4 wt %; from about 3 wt % to about 3.5 wt %; about 9 wt %, about 10 wt %; about 11 wt %, about 12 wt %, about 13 wt %; about 14 wt %, or about 15 wt %, or in any other amount within any of the above ranges.

The presently described topical wound healing compositions may further include a pH adjusting agent, a coloring agent and/or a non-formaldehyde releasing preservative. Each of the described a pH adjusting agent, a coloring agent and/or a non-formaldehyde releasing preservative may be present in the described topical biocompatible compositions in an amount of, for example, from about 00.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01 % to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; from about 3 wt % to about 5 wt %; from about 3 wt % to about 4.5 wt %; from about 3 wt % to about 4 wt %; from about 3 wt % to about 3.5 wt %; about 0.9 wt %; about 1 wt %; or about 1.1 wt %., or in any other amount within any of the above ranges.

The presently described topical wound healing compositions can be free from one or more of the following: gluten; vitamin D; a growth hormone; a paraben; an EU 26 fragrance allergen; and a formaldehyde releasing preservative.

Topical Soothing Composition

The topical soothing composition may be an ointment that provides multi-functional hydration and lipid replenishment to restores disrupted barrier function or otherwise compromised skin. The topical soothing composition may be an anti-irritant that may, for example, suppress inflammatory response to improve comfort during the healing/recovery process. In addition, the topical soothing composition may protect compromised or exposed skin from environmental aggressors.

In addition, the topical soothing composition may encourage cellular regeneration and synthesis of glycosaminoglycans, maintain skin hydration, restores barrier function, calm irritated or otherwise comprised skin, mitigate crusting/scabbing, and/or enhance DNA repair and protection.

The topical soothing composition may include extended release or time released components, including, for example one or more time-release or extended release anti-oxidant components for oxidative stress protection.

The topical soothing composition may include one or more components including, but not limited to, a glycosaminoglycan (GAG) stimulator, an anti-inflammatory, an antioxidant, and a DNA repair component.

The GAG stimulator, which repairs compromised skin, may be any substance that stimulates glycosaminoglycan. For example, the GAG stimulator may be disodium acetyl glucosamine phosphate (DAGP).

The one or more GAG stimulator may be present in the topical soothing composition in of, for example, from >0.01 wt % to about 3 wt %; >0.01 wt % to about 1 wt %; from >0.05 wt % to about 3 wt %; from >0.05 wt % to about 1 wt %; from about 0.05 wt % to about 0.5 wt %; from about 0.07 wt % to about 0.4 wt %; from about 0.08 wt % to about 0.4 wt %; from about 0.08 wt % to about 0.35 wt %; from about 0.08 wt % to about 0.3 wt %; from about 0.08 wt % to about 0.25 wt %; from about 0.09 wt % to about 0.4 wt %; from about 0.09 wt % to about 0.3 wt %; from about 0.09 wt % to about 0.25 wt %; from about 0.1 wt % to about 0.25 wt %; from about 0.11 wt % to about 0.24 wt %; from about 0.12 wt % to about 0.23 wt %; from about 0.13 wt % to about 0.22 wt %; from about 0.14 wt % to about 0.21 wt %; or from about 0.15 wt % to about 0.2 wt %.

Cells synthesize polymers from sugars, particularly GAGs and Hyaluronan from the basis of N-acetyl-glucosamine-6-phosphate (NAG6P). DAGP is a molecule obtained through enzymatic processes and it is not a human growth factor. The disodium moiety of DAGP disassociates releasing N-acetyl-glucosamine-6-phosphate (NAG6P) in skin. GAGs are responsible for aiding the ability of collagen and elastin fibers to retain moisture while Hyaluronan (Hyaluronic Acid) modulates skin moisture balance.

As used in the topical soothing composition herein, administration of a topical composition comprising the GAG stimulation component may increase GAG production by up to 60%, 70%, 80%, 81%, 82%, 83%, 84% or 85% when applied to skin from one to five times a day for a period of up to 10 days, or more. In addition, administration of a topical composition comprising the GAG stimulation component may increase hyaluronic acid synthesis by up to 50%, 75%, 100%, 150%, 200%, 250%, 280%, 281%, 282%, 283%, 284% or 285% from one to five times a day for a period of 0 to 48 hours.

Anti-inflammatory or anti-irritant components used in the topical soothing composition may include, for example, one or more of: Brassica Oleracea (Broccoli) Extract; Helianthus Annuus (Sunflower) Seed Oil; Avena Sativa (Oat) Kernel Flour Protein; and/or Beta-Glucan.

The one or more anti-inflammatories or anti-irritants may be present in the topical soothing composition, either alone or in combination, in an amount of from, for example, from 0.01 wt % to about 30 wt %; from 0.01 wt % to about 25 wt %; from 0.01 wt % to about 20 wt %; from 0.01 wt % to about 15 wt %; 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01 % to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 30 wt %; from 0.1 wt % to about 25 wt %;

from 0.1 wt % to about 20 wt %; from 0.1 wt % to about 15 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about 30 wt %; from 0.5 wt % to about 25 wt %; from 0.5 wt % to about 20 wt %; from 0.5 wt % to about 15 wt %; from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 20 wt %; 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 20; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 30 wt %; from 1 wt % to about 20 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 30 wt %; from about 1.5 wt % to about 20 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 30 wt %; from about 3 wt % to about 20 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; from about 3 wt % to about 5 wt %; from about 3 wt % to about 4.5 wt %; from about 3 wt % to about 4 wt %; from about 3 wt % to about 3.5 wt %; about 1 wt %, about 5 wt %; about 2 wt %, about 3 wt %, about 4 wt %; about 5 wt %, or about 6 wt %, or in any other amount within any of the above ranges.

The one or more antioxidants used in the topical soothing composition may include, for example, one or more antioxidant including, for example, Ubiquinone (Co-Enzyme Q10); Tocopheryl Acetate; Ascorbic Acid; and Retinyl Palmitate. The antioxidant component may include an antioxidant complex that is formulated as a 12-hour time release encapsulate. The antioxidant complex may comprise or consist of Polymethyl Methacrylate and one or more Tocopheryl Acetate, Ascorbic Acid and Retinyl Palmitate, or other suitable antioxidant.

The one or more anti-oxidants may be present in the topical soothing composition, either alone or in combination, in an amount of from, for example, about 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01% to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; from about 3 wt % to about 5 wt %; from about 3 wt % to about 4.5 wt %; from about 3 wt % to about 4 wt %; from about 3 wt % to about 3.5 wt %; or in any other amount within any of the above ranges.

The topical soothing formulation may include of a DNA repair component. The DNA repair component may comprise or consist of one or more of Adenosine Triphosphate, Hydrolyzed Vegetable Protein, Proline, Acetyl Tyrosine, or the like.

The DNA repair component may be may be present in the topical soothing composition, either alone or in combination, in an amount of from >0.01 wt % to about 1 wt %; from >0.05 wt % to about 1 wt %; from about 0.05 wt % to about 0.5 wt %; from about 0.08 wt % to about 0.4 wt %; from about 0.08 wt % to about 0.35 wt %; from about 0.08 wt % to about 0.3 wt %; from about 0.08 wt % to about 0.25 wt %; from about 0.09 wt % to about 0.4 wt %; from about 0.09 wt % to about 0.3 wt %; from about 0.09 wt % to about 0.25 wt %; or from about 0.1 wt % to about 0.25 wt %.

The topical soothing composition may also comprise or consist of one or more absorption promoters, anti-bacterial agents, anti-microbial agents, anti-fungal agents, emollients, self-emulsifying elastomer gels, emulsifiers, solvents, surfactants, preservatives, skin protectants, moisturizers, anti-Inflammatory agents, humectants and/or fragrances.

Each of the absorption promoters, anti-bacterial agents, anti-microbial agents, anti-fungal agents, emollients, self-emulsifying elastomer gels, emulsifiers, solvents, surfactants, preservatives, skin protectants, moisturizers, anti-Inflammatory agents, humectants and/or fragrances may be present in the topical soothing composition in an amount of, for example, about >0.01 wt % to about 1 wt %; from >0.05 wt % to about 1 wt %; from about 0.05 wt % to about 0.5 wt %; from about 0.08 wt % to about 0.4 wt %; from about 0.08 wt % to about 0.35 wt %; from about 0.08 wt % to about 0.3 wt %; from about 0.08 wt % to about 0.25 wt %; from about 0.09 wt % to about 0.4 wt %; from about 0.09 wt % to about 0.3 wt %; from about 0.09 wt % to about 0.25 wt %; from about 0.1 wt % to about 0.25 wt %; from about 0.11 wt % to about 0.24 wt %; from about 0.12 wt % to about 0.23 wt %; from about 0.13 wt % to about 0.22 wt %; from about 0.14 wt % to about 0.21 wt %; from about 0.15 wt % to about 0.2 wt %, about 0.1 wt % to about 5 wt %; from about 0.5 wt % to about 4 wt %; from about 0.5 wt % to about 3 wt %; from about 0.1 wt % to about 3% wt %; from about 0.5 wt % to about 2 wt %; from about 0.5% to about 1.5 wt %, from about 0.1 wt % to about 15 wt %; from about 0.5 wt % to about 10 wt %; from about 1 wt % to about 8 wt %; from about 2 wt % to about 7% wt %; from about 3 wt % to about 6 wt %; from about 2% to about 7 wt %, from about 10 wt % to about 50 wt %; from about 15 wt % to about 45 wt %; from about 20 wt % to about 25 wt %; from about 30 wt % to about 40% wt %; or from about 33 wt % to about 38 wt % 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01% to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; from about 3 wt % to about 5 wt %; from about 3 wt % to about 4.5 wt %; from about 3 wt % to about 4 wt %; from about 3 wt % to about 3.5 wt %; or in any other amount within any of the above ranges.

Epidermal Repair Composition

The epidermal/dermal repair composition may repair, treat or ameliorate the symptoms of compromised skin.

The epidermal/dermal repair composition may comprise or consist of one or more of a skin protectant to protect and relieves dryness and itching due to irritation or otherwise compromised skin. The skin protectant may comprise or consist of colloidal oatmeal.

The skin protectant may be present in the epidermal/dermal repair compositions in an of, for example, 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01% to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; from about 3 wt % to about 5 wt %; from about 3 wt % to about 4.5 wt %; from about 3 wt % to about 4 wt %; from about 3 wt % to about 3.5 wt %; or in any other amount within any of the above ranges.

Peptides may be included in the epidermal/dermal repair composition. For example, Tetrapeptide-21 enhances extracellular matrix (ECM) protein expression when used in the epidermal/dermal repair composition. Tetrapeptide-21 also stimulates Collagen 1, Fibronectin and hyaluronic acid in the skin leading to re-epithelialization and accelerated healing. Myristoyl Pentapeptide-11 encourages cell proliferation to speed skin recovery.

One or more peptide or compositions comprising a peptide may be present in the epidermal repair compositions in an amount of, for example, 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01% to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; or in any other amount within any of the above ranges.

The epidermal/dermal repair composition may also include a moisturizer. The moisturizer may comprise or consist of glycerin to replenish, hydrate and minimize transepidermal water loss (TEWL). Either with glycerin or alone, the moisturizing component may also include one or more of propylene glycol, ceramides, shea butter, jojoba oil, cocoa butter or avocado oil.

The one or more moisturizer may be present in the epidermal/dermal repair composition, alone or in combination, in an amount of in an amount of, for example, 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01% to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2 wt %; from about 0.5 wt % to about 1.5 wt %; from about 0.5 wt % to about 1 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; or in any other amount within any of the above ranges.

One or more anti-inflammatory agent may also be included in the epidermal/dermal repair composition to calm redness and sooth irritated or otherwise compromised skin. The one or more moisturizer may be present in the epidermal/dermal repair composition, alone or in combination, in an amount of in an amount of, for example, about 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01% to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1 to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from 1 wt % to about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; from about 3 wt % to about 5 wt %; from about 3 wt % to about 4.5 wt %; from about 3 wt % to about 4 wt %; from about 3 wt % to about 3.5 wt %; or in any other amount within any of the above ranges.

The epidermal/dermal repair composition may include one or more antioxidants or an antioxidant complex. The one or more antioxidant used in the topical soothing composition may include, for example, one or more of: Ubiquinone (Co-Enzyme Q10); Tocopheryl Acetate; Ascorbic Acid; and Retinyl Palmitate. The antioxidant complex may be formulated as a 12-hour time release encapsulate. The antioxidant complex may comprise or consist of Polymethyl Methacrylate and one or more Tocopheryl Acetate, Ascorbic Acid and Retinyl Palmitate, or other suitable antioxidant.

The one or more anti-oxidants may be present in the epidermal/dermal repair composition, either alone or in combination, in an amount of from, for example, 0.01 wt % to about 10 wt %; from 0.01 wt % to about 9 wt %; from 0.01 wt % to about 8 wt %; from 0.01 wt % to about 7 wt %; from 0.01 wt % to about 6 wt %; from 0.01 wt % to about 5 wt %; from 0.01 wt % to about 4.5 wt %; from 0.01 wt % to about 4 wt %; from 0.01 wt % to about 3.5 wt %; from 0.01 wt % to about 3 wt %; from 0.01 wt % to about 2.5 wt %; from 0.01 wt % to about 2 wt %; from 0.01 wt % to about 2.25 wt %; from 0.01 wt % to about 2 wt %; from about 0.01 % to about 4 wt %; from about 0.01 wt % to about 3 wt %; from about 0.01 wt % to about 2.5 wt %; from about 0.01 wt % to about 2.25 wt %; from about 0.01 wt % to about 2 wt %; from about 0.01 wt % to about 1.5 wt %; from about 0.01 wt % to about 1 wt %; from about 0.01 wt % to about 0.5 wt %; from 0.1 wt % to about 10 wt %; from 0.1 wt % to about 9 wt %; from 0.1 wt % to about 8 wt %; from 0.1 wt % to about 7 wt %; from 0.1 wt % to about 6 wt %; from 0.1 wt % to about 5 wt %; from 0.1 wt % to about 4.5 wt %; from 0.1 wt % to about 4 wt %; from 0.1 wt % to about 3.5 wt %; from 0.1 wt % to about 3 wt %; from 0.1 wt % to about 2.5 wt %; from 0.1 wt % to about 2 wt %; from 0.1 wt % to about 2.25 wt %; from 0.1 wt % to about 2 wt %; from about 0.1% to about 4 wt %; from about 0.1 wt % to about 3 wt %; from about 0.1 wt % to about 2.5 wt %; from about 0.1 wt % to about 2.25 wt %; from about 0.1 wt % to about 2 wt %; from about 0.1 wt % to about 1.5 wt %; from about 0.1 wt % to about 1 wt %; from about 0.1 wt % to about 0.5 wt %; from 0.25 wt % to about 30 wt %; from 0.25 wt % to about 25 wt %; from 0.25 wt % to about 20 wt %; from 0.25 wt % to about 15 wt %; 0.25 wt % to about 10 wt %; from 0.25 wt % to about 9 wt %; from 0.25 wt % to about 8 wt %; from 0.25 wt % to about 7 wt %; from 0.25 wt % to about 6 wt %; from 0.25 wt % to about 5 wt %; from 0.25 wt % to about 4.5 wt %; from 0.25 wt % to about 4 wt %; from 0.25 wt % to about 3.5 wt %; from 0.25 wt % to about 3 wt %; from 0.25 wt % to about 2.5 wt %; from 0.25 wt % to about 2 wt %; from 0.25 wt % to about 2.25 wt %; from 0.25 wt % to about 1.75 wt %; from 0.5 wt % to about from 0.5 wt % to about 10 wt %; from 0.5 wt % to about 9 wt %; from 0.5 wt % to about 8 wt %; from 0.5 wt % to about 7 wt %; from 0.5 wt % to about 6 wt %; from 0.5 wt % to about 5 wt %; from 0.5 wt % to about 4.5 wt %; from 0.5 wt % to about 4 wt %; from 0.5 wt % to about 3.5 wt %; from 0.5 wt % to about 3 wt %; from 0.5 wt % to about 2.5 wt %; from 0.5 wt % to about 2 wt %; from 0.5 wt % to about 2.25 wt %; from 0.5 wt % to about 2 wt %; from about 0.5% to about 4 wt %; from about 0.5 wt % to about 3 wt %; from about 0.5 wt % to about 2.5 wt %; from about 0.5 wt % to about 2.25 wt %; from about 0.5 wt % to about 2 wt %; from about 0.5 wt % to about 1.5 wt %; from about 0.5 wt % to about 1 wt %; from 0.7 wt % to about 10 wt %; from 0.7 wt % to about 9 wt %; from 0.7 wt % to about 8 wt %; from 0.7 wt % to about 7 wt %; from 0.7 wt % to about 6 wt %; from 0.7 wt % to about 5 wt %; from 0.7 wt % to about 4.5 wt %; from 0.7 wt % to about 4 wt %; from 0.7 wt % to about 3.5 wt %; from 0.7 wt % to about 3 wt %; from 0.7 wt % to about 2.5 wt %; from 0.7 wt % to about 2 wt %; from 0.7 wt % to about 2.25 wt %; from 0.7 wt % to about 2 wt %; from about 0.7% to about 4 wt %; from about 0.7 wt % to about 3 wt %; from about 0.7 wt % to about 2.5 wt %; from about 0.7 wt % to about 2.25 wt %; from about 0.7 wt % to about 2 wt %; from about 0.7 wt % to about 1.5 wt %; from about 0.7 wt % to about 1 wt %; from 0.9 wt % to about 10 wt %; from 0.9 wt % to about 9 wt %; from 0.9 wt % to about 8 wt %; from 0.9 wt % to about 7 wt %; from 0.9 wt % to about 6 wt %; from 0.9 wt % to about 5 wt %; from 0.9 wt % to about 4.5 wt %; from 0.9 wt % to about 4 wt %; from 0.9 wt % to about 3.5 wt %; from 0.9 wt % to about 3 wt %; from 0.9 wt % to about 2.5 wt %; from 0.9 wt % to about 2 wt %; from 0.9 wt % to about 2.25 wt %; from 0.9 wt % to about 2 wt %; from about 0.9% to about 4 wt %; from about 0.9 wt % to about 3 wt %; from about 0.9 wt % to about 2.5 wt %; from about 0.9 wt % to about 2.25 wt %; from about 0.9 wt % to about 2 wt %; from about 0.9 wt % to about 1.5 wt %; from about 0.9 wt % to about 1 wt %; from 1 wt % to about 10 wt %; from 1 wt % to about 9 wt %; from 1 wt % to about 8 wt %; from 1 wt % to about 7 wt %; from 1 wt % to about 6 wt %; from 1 wt % to about 5 wt %; from 1 wt % to about 4.5 wt %; from 1 wt % to about 4 wt %; from 1 wt % to about 3.5 wt %; from 1 wt % to about 3 wt %; from 1 wt % to about 2.5 wt %; from 1 wt % to about 2 wt %; from 1 wt % to about 2.25 wt %; from 1 wt % to about 2 wt %; from about 1% to about 4 wt %; from about 1 wt % to about 3 wt %; from about 1 wt % to about 2.5 wt %; from about 1 wt % to about 2.25 wt %; from about 1 wt % to about 2 wt %; from about 1 wt % to about 1.5 wt %; from about 1.5 wt % to about 10 wt %; from about 1.5 wt % to about 9 wt %; from about 1.5 wt % to about 8 wt %; from about 1.5 wt % to about 7 wt %; from about 1.5 wt % to about 6 wt %; from about 1.5 wt % to about 5 wt %; from about 1.5 wt % to about 4.5 wt %; from about 1.5 wt % to about 4 wt %; from about 1.5 wt % to about 3.5 wt %; from about 1.5 wt % to about 3 wt %; from about 1.5 wt % to about 2.5 wt %; %; from about 1.5 wt % to about 2.25 wt %; from about 1.5 wt % to about 2 wt %; from about 3 wt % to about 10 wt %; from about 3 wt % to about 9 wt %; from about 3 wt % to about 8 wt %; from about 3 wt % to about 7 wt %; from about 3 wt % to about 6 wt %; from about 3 wt % to about 5 wt %; from about 3 wt % to about 4.5 wt %; from about 3 wt % to about 4 wt %; from about 3 wt % to about 3.5 wt %; or in any other amount within any of the above ranges.

Optionally, the epidermal/dermal repair composition may also include one or more of a carrier, a solvent, a thickening agent, a humectant, an emulsifier, anti-bacterial agents, anti-microbial agents, anti-fungal agents, an emollient, an emulsifying agent, a skin protectant active, a neutralizing agent, a preservative, a collagen Stimulator, a DNA protector, a moisturizing agent, soy phospholipids, a DNA repairing agent and a skin conditioning agent.

Each of the one or more of a carrier, solvent, thickening agent, humectant, emulsifier, anti-bacterial agents, anti-microbial agents, anti-fungal agents, emollient, emulsifying agent, skin protectant active, neutralizing agent, preservative, collagen Stimulator, DNA protector, moisturizing agent, soy phospholipids, DNA repairing agent and skin conditioning agent may be present in the epidermal/dermal repair composition in any amount, including, for example, about >0.01 wt % to about 1 wt %; from >0.05 wt % to about 1 wt %; from about 0.05 wt % to about 0.5 wt %; from about 0.08 wt % to about 0.4 wt %; from about 0.08 wt % to about 0.35 wt %; from about 0.08 wt % to about 0.3 wt %; from about 0.08 wt % to about 0.25 wt %; from about 0.09 wt % to about 0.4 wt %; from about 0.09 wt % to about 0.3 wt %; from about 0.09 wt % to about 0.25 wt %; from about 0.1 wt % to about 0.25 wt %; from about 0.11 wt % to about 0.24 wt %; from about 0.12 wt % to about 0.23 wt %; from about 0.13 wt % to about 0.22 wt %; from about 0.14 wt % to about 0.21 wt %; from about 0.15 wt % to about 0.2 wt %, about 0.1 wt % to about 5 wt %; from about 0.5 wt % to about 4 wt %; from about 0.5 wt % to about 3 wt %; from about 0.1 wt % to about 3% wt %; from about 0.5 wt % to about 2 wt %; from about 0.5 % to about 1.5 wt %, from about 0.1 wt % to about 15 wt %; from about 0.5 wt % to about 10 wt %; from about 1 wt % to about 8 wt %; from about 2 wt % to about 7% wt %; from about 3 wt % to about 6 wt %; from about 2% to about 7 wt %, from about 10 wt % to about 50 wt %; from about 15 wt % to about 45 wt %; from about 20 wt % to about 25 wt %; from about 30 wt % to about 40% wt %; or from about 33 wt % to about 38 wt %.

Each of the aforementioned topical biocompatible compositions may also include known biocompatible carriers, excipients, fillers, and diluents are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, the contents of all of which are hereby incorporated by reference in their entirety.

These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990) and Remington's Pharmaceutical Sciences, 18th Ed., Mack Publishing Co., Easton, Pa. (1990), both of which are incorporated by reference herein in their entirety.

All of the presently described topical biocompatible compositions herein can be formulated as one or more of the following: a powder, a solution, an emulsion, a gel, a cream, a lotion, an ointment, a foam, an aerosol, and a serum.

Methods of Treatment

The presently described topical biocompatible compositions include topical wound healing compositions, topical soothing compositions and epidermal/dermal repair compositions. Also provided herein are methods of using the biocompatible compositions for treating skin conditions. Non-limiting conditions that may be treated by the topical administration of the present compositions include, but are not limited to, one or more of the following: compromised skin; post-procedure skin; skin irritation; skin inflammation; skin damage; burns to the skin; and skin sunburn.

Post-procedure skin is skin that has be subjected to a procedure that can include but is not limited to, a resurfacing procedure, a chemical peel, ablative laser treatment ($CO_2$ lasers), non-ablative laser treatment, non-laser light-based treatments (IPL, infrared treatments), radio-frequency based treatments, dermabrasion, dermaplaning, or any combination thereof.

Compromised skin, post-procedure skin, burned skin, and/or damaged skin, can exhibit one or more of skin irritation, skin inflammation, swelling, redness, scabbing, and pain.

Skin irritation and/or skin inflammation can be caused by one or more of: a procedure; an allergic reaction; contact with a skin irritant such as poison ivy, poison oak, poison sumac, an insect bite, soaps, detergents, cosmetics, and/or metals (metal jewelry); a fungal infection; a skin treatment such as acne treatment (e.g., a retinol); and trauma.

The methods of treating skin conditions described herein may comprise or consist of topically administering one or more of the described biocompatible compositions to a subject in need thereof.

The topical biocompatible compositions may be provided in a kit to treat post-procedure, or otherwise compromised skin. The kit may include the topical wound healing composition and/or the topical soothing composition and/or the epidermal/dermal repair composition. Thus, provided is a method of treating a subject with post-procedure, or otherwise compromised skin by administering a topical wound healing composition as provided herein. The method may further comprise, administering a topical soothing composition provided herein and/or an epidermal repair composition as provided herein.

Dosage

The presently described biocompatible topical compositions can be topically administered in any form. A sufficient amount of the topical composition can be applied onto the affected area and surrounding skin, for example, in an amount sufficient to cover an affected area plus a margin of healthy skin or tissue surrounding the affected area, if possible, for example, a margin of about 0.5 inches. The compositions can be applied to any skin surface, including for example, facial skin, and the skin of the hands, neck, and/or chest.

The compositions can be applied in a single, one-time application, once a week, once a bi-week, once a month, or from one to four times daily, for a period of time sufficient to alleviate symptoms, for example, for a period of time of one week, from 1 to 12 weeks or more, from 1 to 6 weeks, from 2 to 12 weeks, from 2 to 12 weeks, from 2 to 8 weeks, from 2 to 6 weeks, from 2 to 4 weeks, from 4 to 12 weeks, from 4 to 8 weeks, or from 4 to 6 weeks. The present compositions can be administered, for example, at a frequency of once per day or twice per day. The presently described compositions can be topically administered once per day for a period of time from 1 week to 4 weeks, of from 1 week to 2 weeks, for 1 week, for 2 weeks, for 3 weeks, for 4 weeks, or for 4 weeks or more.

The presently described compositions can be applied in a therapeutically effective amount, for example, an amount sufficient to cover an affected area plus a margin of healthy skin or tissue surrounding the affected area, for example, a margin of about 0.5 inches. Suitable amounts, for example, per application per affected area or cumulative daily dosage per affected area (for example two applications in a 24 hour period), can include, for example, from about 0.1 grams to about 6 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 1.5 grams; from about 0.5 grams to about 4.5 grams; 5 grams to about 4 grams; 0.5 grams to about 3.5 grams; 0.5 grams to about 3 grams; 0.5 grams to about 2.5 grams; 0.5 grams to about 2 grams; 0.5 grams to about 1 gram; about 0.5 grams; about 1 gram; about 1.5 grams; about 2 grams; about 2.5 grams; or about 3 grams.

If desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

The biocompatible compositions may be given in a single or multiple doses per time period, for example, daily, weekly, bi-weekly, or monthly. In an embodiment, the biocompatible compositions can be given from one to four times per period. In another embodiment, the present compositions may be given once per week, for a period of from one to six weeks, for example for one week, for two weeks, for three weeks, for four weeks, five weeks, or for six weeks.

It is understood, however, that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; the area to be treated and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

The optimal biocompatible formulations will be determined by one skilled in the art depending upon considerations such as the particular active agent combination and the desired dosage. See, for example, "*Remington's Pharmaceutical Sciences*", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the essential lipids.

The present biocompatible topical composition in accordance with the subject matter described herein may be a topical dosage form packaged in, for example, a multi-use or single-use package, including for example, a tube, a tottle, a pump, a container or bottle, a vial, a jar, a packet, or a blister package.

Single dosage kits and packages containing once per day amount of the biocompatible composition may be prepared.

Single dose, unit dose, and once-daily disposable containers of the present biocompatible compositions are contemplated as within the scope of the present subject matter.

The present biocompatible compositions remain stable in storage for periods including up to about 5 years, between about 3 months and about 5 years, between about 3 months and about 4 years, between about 3 months and about 3 years, and alternately any time period between about 6 months and about 3 years.

The presently described biocompatible composition in accordance with the subject matter described herein remains stable for up to at least 3 years at a temperature of less than or equal to 40° C. In an embodiment, the presently described topical formulation remains stable for at least 2 years at a temperature of less than or equal to 40° C. In an embodiment, the presently described biocompatible composition remains stable for at least 3 years at a temperature of less than or equal to 40° C. and at a humidity of up to 75% RH, for at least 2 years at a temperature of less than or equal to 40° C. and at a humidity of up to 75% RH, or for at least 3 years at a temperature of less than or equal to 30° C. and at a humidity of up to 75% RH. In a further embodiment, the presently described biocompatible composition in accordance with the subject matter described herein remains stable for an extended period of time when packaged in a multi-use container such as a bottle, and exhibits equal to or even greater stability when packaged in a single-use package such as a blister package.

EXAMPLES

The following examples are illustrative of the present biocompatible compositions and are not intended to be limitations thereon.

Example 1

Astringent Powder

A. Formulation

According to the present subject matter, a topical healing composition was formulated as set forth in Table 1 below:

TABLE 1

TOPICAL HEALING COMPOSITION FORMULATION

| Ingredient | Supplier | Generic Description | % By Weight | Function |
| --- | --- | --- | --- | --- |
| Dextrin #D E137 | (Spectrum) | complex branched glucan | 12.4000 | Filler/Carrier |
| Calcium Acetate #C1065 | (Spectrum) | calcium salt of acetic acid | 33.6000 | Astringent; Skin Protectant |
| OriStar ALSF-14 | (Orient Stars) | Aluminum sulfate | 47.5000 | Astringent; Skin Protectant |
| Tech-0 #11-080 | (Beacon CMP) | Avena Sativa (Oat) Kernal Protein USP | 3.0000 | Anti-inflammatory; Calm/Soothe |
| Clarisoy 100 | (ADM) | Soluble soy protein | 1.5000 | Antioxidant/Anti-inflammatory |
| Avonlac 182 | (Glanbia) | whey protein concentrate, 80% protein | 1.0000 | Inflammatory Modulation; Healing |
| OriStar Chitosan | (Orient Stars) | Linear polymer of beta(1-4) linked glucosamine | 0.5000 | Hydrating Wound Dress; Prevent Scabbing/Crusting |
| Potassium Sorbate, FCC | (Univar) | Potassium sorbate | 0.5000 | Anti-Fungal/Antibacterial |

B. Method of Manufacture

In order to prepare the astringent set forth above, a 1,000 lb. bulk mixture is prepared by combining the ingredients, in dry powder form, in the amounts set forth in Table 2 below and blending the same until a uniform mixture was achieved. Once the uniform mixture is achieved the bulk uniform mixture may be sieved through a mesh screen to break-up any clumps.

TABLE 2

Bulk Mixture-Healing Composition

| Ingredient | By Weight (lbs.) |
| --- | --- |
| Dextrin #DE137 | 124.0000 |
| Calcium Acetate #C1065 | 336.0000 |
| OriStar ALSF-14 | 475.0000 |
| Tech-0 #11-080 | 30.0000 |
| Clarisoy 100 | 15.0000 |
| Avonlac 182 | 10.0000 |
| OriStar Chitosan | 5.0000 |
| Potassium Sorbate, FCC | 5.0000 |
| | 1,000.0000 lbs. |

The astringent powder of Example 1 has the following properties:

TABLE 3

Properties-Healing Composition

| | |
| --- | --- |
| Color: | Off-white (to match standard) |
| Odor: | Characteristic (to match standard) |
| Appearance: | Flowable powder with some crystalline particles present |
| $pH_c$ 25° C.: (1% turbid solution) | 4.0-4.8 |
| Total Aerobic Plate Count: | less than 100 cfu per gram (Including Yeast & Mold) |
| Gram Negative Bacteria: | Absent |
| Assay: Calcium Acetate, Monohydrate | 30.15%-36.85% |
| Aluminum Sulfate, Tetradecahydrate | 42.75%-52.25% |

Example 2

Topical Soothing Composition

A. Formulation

According to the present subject matter, a topical soothing composition was formulated as set forth in Table 4 below:

TABLE 4

TOPICAL SOOTHING COMPOSITION

| Ingredient | Supplier | Generic Description | % By Weight | Function |
|---|---|---|---|---|
| Softisan 378 | (Cremer/ Sasol) | Caprylic and Capric and Myristic and Stearic Triglycerides | 13.0000 | Absorption promoter |
| Panalane L-14E | (Lipo) | Hydrogenated Polyisobutene | 23.0000 | Emollient |
| Syncrowax HRC PA (MH) | (Croda) | Tribehenin | 3.5000 | Carrier |
| KSG-330 | (Chemtec) | PEG-15/Lauryl Dimethicone Crosspolymer | 5.0000 | self-emulsifying elastomer gel |
| Abil WE 09 | (Evonik) | Polyglyceryl-4 Isostearate (and) Cetyl PEG/PPG 10/1 Dimethicone (and) Hexyl Laurate | 3.0000 | Emulsifier |
| Bronidox 1160 | (BASF) | 2-Phenoxyethanol | 0.7000 | Solvent |
| Deionized Water | (Mfr.) | Water | 36.5500 | Carrier/Solvent |
| Magnesium Sulfate, USP | (Mfr.) | Magnesium Sulfate | 0.7000 | Surfactant |
| Glycerin, 99.7% USP | (Mfr.) | Glycerin | 5.0000 | Humectant |
| Germazide C | (BASF) | Chlorphenesin | 0.1500 | anti-fungal, antibacterial preservative |
| Uniprotect PT-3 | (Induchem) | Panthenyl Triacetate (and) Ethyl Linoleate (and) Oleyl Alcohol (and) Tocopherol | 0.7500 | DNA Protection/Repair |
| All-Q (Coenzyme Q10) Plus | (DSM) | Coenzyme Q 10 and Vitamin E acetate in a cosmetic carrier oil | 0.2000 | Skin protectant; cellular regeneration; smoothing wrinkles |
| Actiphyte of Broccoli Lipo Sun Special | (Active Organics) | Brassica Oleracea Italica (Broccoli) Extract | 3.0000 | Anti-inflammatory |
| Tech 0 11-070 | (Beacon) | Avena sativa (Oat) Kernel Flour | 0.5000 | Skin Protectant/Soothing agent |
| DC ACE #D1006 | (Resources of Nature) | Polymethacrylate (and) Tocopheryl Acetate (and) Ascorbic Acid (and) Retinyl Palmitate; 12 hour delayed release formulation | 1.0000 | Anti-Oxidant |
| Unirepair T-43 | (Induchem) | Butylene Glycol (and) Acetyl Tyrosine (and) Proline (and) Hydrogenated Vegetable Protein (and) Adenosine Triphosphate (and) water | 0.2500 | Skin protectant |
| Novhyal Biotech G | (Induchem) | Glycerin (and) Disodium Acetyl Glucosamine Phosphate | 0.2000 | Anti-aging/GAG stimulator |
| Aqualance | (Sederma/Croda) | Erythritol (and) Homarine HCl | 1.0000 | skin moisturizer |
| BP Glucan MC | (Jeen) | Beta Glucan | 2.0000 | Anti-Inflammatory Agent |
| DL Biomoist 1% | (Deveraux) | 1% solution of Sodium Hyaluronate in water | 0.2500 | Skin moisturizer and humectant |
| Fragrance Aromatonic S13-67172 | (Premier) | Fragrance | 0.2500 | Fragrance |

B. Method of Manufacture

To prepare the topical soothing composition set forth above, a 1,000 lb. bulk mixture was prepared by combining the ingredients set forth in part A of Table 5, shown below, into a main mixing vessel and heating the contents to about 70° C. The heated product is agitated until the resulting mixture product is uniform. In a separate tank, the ingredients listed in Part B of Table 5 are combined and heated to about 70° C. Once heated, the contents of the separate tank, which includes the ingredients in Part B, are added to the main mixing vessel and homogenized for 15 minutes until smooth and uniform. The mixture is cooled to 45° C. The ingredients listed in part C are added, in any order, or in the specific order listed, to the main mixture vessel, which includes the ingredients from parts A and B. Each ingredient from Part C is added under mixture/agitation and mixed well until it is smooth and uniform. The mixture is cooled to 35° C.

TABLE 5

Bulk Mixture-Topical Soothing Composition

| Ingredient | By Weight (lbs.) |
|---|---|
| Part A | |
| Softisan 378 | 130.0000 |
| Panalane L-14E | 230.0000 |
| Syncrowax HRC PA(MH) KSG-330 | 35.0000 |
| Abil WE 09 | 50.0000 |
| Bronidox | 7.0000 |
| Part B | |
| Deionized Water | 365.5000 |
| Magnesium Sulfate, USP | 7.0000 |
| Glycerin, 99.7% USP | 50.0000 |
| Germazide C | 1.5000 |
| Part C | |
| Uniprotect PT-3 | 7.5000 |
| All-Q (Coenzyme Q10) Plus | 2.0000 |
| Actiphyte of Broccoli Lipo Sun Special | 30.0000 |
| Tech 0 11-070 | 5.0000 |
| DC ACE | 10.0000 |
| Unirepair T-43 | 2.5000 |
| Novhyal Biotech G | 2.0000 |
| Aqualance | 10.0000 |
| BP Glucan MC | 20.0000 |
| DL Biomoist 1% | 2.5000 |
| Fragrance Aromatonic S13-67172 | 2.5000 |
| | 100.0000 |

The soothing composition of Example 2 has the following properties:

TABLE 6

Properties-Soothing Ointment

| | |
|---|---|
| Color: | Yellow (to match standard) |
| Odor: | Characteristic (to match standard) |
| Appearance: | Shiny, opaque, semi-viscous emulsion |
| pH @ 25° C.: | N/A |
| Specific Gravity @ 25/25° C.: | 0.94 ± 0.02 |
| Viscosity (cps) @ 25° C.: | 10,000-20,000 (INITIAL) |
| (RVT: #6 spindle @ 10 rpm) | 25,000-40,000 (AT 24 HOURS) |
| Total Aerobic Plate Count: (Including Yeast & Mold) | Less than 100 cfu per ml |
| Gram Negative Bacteria: | Absent |
| IR: | To match standard |
| % Solids: | 44.0% ± 2.0% |

Example 3

Epidermal Repair Composition

A. Formulation

According to the present subject matter, an epidermal/dermal repair cream was formulated to have the following set forth in Table 7 below:

TABLE 7

| Ingredient | Supplier | Generic Description | % By Weight | Function |
|---|---|---|---|---|
| Part A | | | | |
| Deionized Water | (Mfg.) | Water, Aqua, Eau | 71.7800 | Diluent/Solvent |
| Carbopol Ultrez-20 | (Lubrizol) | Acrylates/C10-30 Alkyl Acrylate Crosspolymer | 0.3000 | Thickener |
| Glycerin, USP | (Nexeo) | Glycerin | 4.0000 | Hydrator/Barrier restoration |
| Brij S721-S0-(AP) | (Croda) | polyoxyethylene fatty ethers derived from stearyl alcohols | 0.5000 | Emulsifier |
| Part B | | | | |
| Simulsol 165 | (Seppic) | Glyceryl Stearate (and) PEG-100 Stearate | 3.5000 | Emulsifier |
| Lanette 16 | (BASF) | Cetyl Alcohol | 2.0000 | Thickening/Emulsifiying Agent |
| Schercemol 318 | (Lubrizol) | Isopropyl Isostearate | 5.0000 | Emulsifier |
| Snow White Petrolatum USP | (Calumet) | White Petrolatum | 4.0000 | Lipid Replenishment/Barrier Restoration |
| Refined Shea Butter | (Ashland) | Butyrospemum Parkii (Shea Butter) | 2.0000 | Lipid Replenishment/Barrier Restoration |
| Xiameter PMX-200, 1000cs | (Xiameter) | Dimethicone | 2.0000 | Barrier Protection |
| Part C | | | | |
| AMP Ultra PC 2000 | (Angus) | Aminomethyl Propanol | 0.1200 | Neutralizing Agent; pH adjuster |
| Part D | | | | |
| Tech-0 #11-065 | (Beacon CMP) | Avena Sativa (Oat) Kernel Meal | 1.0000 | Skin Protectant/Soothing Agent |

TABLE 7-continued

| Ingredient | Supplier | Generic Description | % By Weight | Function |
|---|---|---|---|---|
| Tego-Pep 4-17 | (Evonik) | Water (and) Butylene Glycol (and) Glycerin (and) Tetrapeptide-21 | 0.2500 | Re-Epithelization |
| DC ACE #D1006 | (Resources of Nature) | Polymethacrylate (and) Tocopheryl Acetate (and) Ascorbic Acid (and) Retinyl Palmitate; 12 hour delayed release formulation | 0.5000 | Anti-oxidant |
| BP Glucan-MC | (Jeen) | Beta Glucan | 2.0000 | Anti-Inflammatory Agent |
| Sympeptide 225 (694269) | (Symrise) | Glycerin (and) Water (and) Myristoyl Pentapeptide-11 | 0.2500 | FGF/Collagen Stimulation; Cell Proliferation (Matrix Remodeling, Tissue repair, Wound Healing) |
| Stepanquat 50 NF | (Stepan) | n-alkyl dimethyl benzyl ammonium chloride | 0.2000 | Preservative |
| Benzyl Alcohol | (Spectrum) | Benzyl Alcohol | 0.6000 | Preservative |

B. Method of Manufacture

To prepare the epidermal/dermal repair cream set forth above, the Carbopol was hydrated in a first vessel. The remaining ingredients listed in Part A were added to the main vessel and heated to about 75° C. and mixed until uniform. In a second vessel, the ingredients listed in Part B was combined and heated to about 75° C. and mixed until completely melted and uniform. The mixture from the second vessel was added to the first vessel and the resulting mixture was mixed until uniform. The ingredients listed in Part C were added to the mixture in the first vessel and mixed for about 20 minutes, until uniform. The resulting mixture was cooled to 45° C. Once 45° C. is reached, the ingredients listed in Part D were added to the mixture in the first vessel. The ingredients were added in the order listed and after each ingredient was added, the mixture was mixed well until substantially uniform. Once uniform, the resulting mixture was cooled to 35° C.

The epidermal repair composition protectant of Example 3 has the following properties:

TABLE 8

| Properties-Epidermal/Dermal Repair Composition | |
|---|---|
| APPEARANCE: | Light beige, shiny, smooth, opaque |
| pH @ 25° C.: | viscous cream 5.32 |
| VISCOSITY @ 25° C. ( RVT: #TD spindle @ 5 | 80,000 (Initial) |

Example 4

In order to evaluate the effectivesness of present compositions and kits, a side-by-side analysis, comparing the present compositions and methods to previously know compositions for post procedure healing was conducted. Specifically, following a 25% trichloroacetic acid ("TCA") peel, a 50-year-old female patient was instructed to apply the compositions according to the present subject matter to the right side of her face and comparative compositions to the left side of her face.

The patient was previously diagnosed with Fitzpatrick Skin Type III and significant sun exposure with actinic damage, solar dyschromia, fine lines and general signs of aging. The patient was monitored by her dermatologist for inflammation, surface skin peeling, crusting, re-epithelialization, patient discomfort and overall patient experience.

Immediately following a 25% TCA facial peel, the patient was treated with a viscous lidocaine mixed with a medical grade copper peptide to provide an anesthetic effect and reduce discomfort. The patient was instructed to use a mild, medical cleanser on her full face. The patient was also provided two post-procedure systems and was told to use the post procedure compositions described in Examples 1-3 on the right side of her face and use a different commercially available post-procedure system on the left side the morning after the TCA peel.

With specific regard to the presently described compositions, the composition of Example 1 was administered as described herein above for the first five (5) days post-procedure. In addition, the composition of Example 2 was also administered as set forth herein above for the above for the first 5 days post-procedure. The composition of Example 3 was administered from days 5 to 15 post procedure.

The comparative compositions, SkinMedica® Restorative Ointment and SkinMedica® TNS Ceramide Treatment Cream were administered to the opposite side of the patient's face. Each of the comparative products were administered according to the manufacturer's instructions under the supervision of a dermatologist.

FIG. 1 shows a frontal view of the patient's entire face pre-procedure. As shown, prior to the TCA peel, the patient exhibits generally normal skin for a subject with her diagnosis.

On the second post-operative day, the physician examined the patient to evaluate the two treatments and associated protocols. As shown in FIG. 2A, the early peeling and re-epithelialization was observed on the right side of the patient's face, which was subject to the compositions of Examples 1 and 2 respectively. In contrast, as shown in FIG. 2B, no peeling was observed on the left side of the face, which was subject to the SkinMedica® Restorative Ointment. Additionally, the right side of the face was less swollen and more lifted then the left, comparative side.

Figure 3A:
FIG. 3A shows the right side profile view of patient five (5) days post chemical peel after instructed use of the present post-procedure biocompatible topical compositions.
Figure 3B:
FIG. 3B shows the left side view of the same patient on the same day after instructed use of a comparative post procedure topical regime.

At day five, on exam and as shown in FIG. 3A more significant epithelialization, less crusting and reduced swelling was observed on the right side of the face than on day 2. As shown in FIG. 3B, the left side of the face, treated with the comparative composition, exhibited less epithelialization, more retained crusting and slower healing. Additionally, the patient reported feeling less irritation, discomfort, dryness and pruritis on the right side of her face as compared to her left side.

Figure 4A:
FIG. 4A shows the right side profile view of patient nine (9) days post chemical peel after instructed use of the present post-procedure biocompatible topical compositions.
Figure 4B:
FIG. 4B shows the left side view of the same patient on the same day after instructed use of a comparative post procedure topical regime.

On the ninth day post-procedure, the patient was again evaluated by her dermatologist. As shown in FIG. 4A, the lateral corners of the mouth were less red on the right side when compared to the left side, which is shown in FIG. 4B. In addition, the right side showed no scabbing, and near complete re-epithelialization, and was overall less red than the left side. The left (comparative) side had more crusting and showed scabbing on the chin.

While both post-procedure recovery systems included calming, hydration and epidermal stimulation ingredients, their formulations and protocols were different. Based on examinations on days 2, 5 and 9, the side of the patient's face showing more rapid peeling, earlier re-epithelialization, less swelling and irritation was the side to which the compositions of Examples 1-3 were administered. Accordingly, when compared to similar compositions, and treatment protocols, post-procedure administration of the compositions of Examples 1-3 lead to quicker healing and a more positive patient experience.

All publications cited in the specification are indicative of the level of skill of those skilled in the art to which the presently described subject matter pertains. All of these publications are hereby incorporated by reference herein to the same extent as if each individual publication were specifically and individually indicated as being incorporated by reference.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A topical wound healing composition, consisting essentially of:
   aluminum sulfate tetradecahydrate present in an amount of from about 40.0 wt % to about 55.0 wt % based on the weight of the topical wound healing composition,
   calcium acetate monohydrate present in an amount of from about 28.0 wt % to about 39.0 w t% based on the weight of the topical wound healing composition,
   avena sativa kernel protein present in an amount of from about 0.01 wt % to about 20 wt % based on the weight of the topical wound healing composition,
   soy protein in an amount of from about 0.01 wt % to about 20 wt % based on the weight of the topical wound healing composition, and
   whey protein present in an amount of from about 0.01 wt % to about 20 wt % based on the weight of the topical wound healing composition;
   chitosan present in an amount of from about 0.25 wt % to about 50 wt % based on the weight of the topical wound healing composition;
   potassium sorbate present in an amount of from about 0.25 wt % to about 10 wt % based on the weight of the topical wound healing composition; and
   dextrin present in an amount of from about 5 wt % to about 50 wt % based on the weight of the topical wound healing composition.

2. The wound healing composition of claim 1, wherein the avena sativa kernel protein present in an amount of from about 1.5 wt % to about 4.5 wt % based on the weight of the wound healing compostion.

3. The wound healing composition of claim 1, wherein the soy protein present in an amount of from about 0.5 wt % to about 2.5 wt % based on the weight of the the wound healing compostion.

4. The wound healing composition of claim 1, wherein the whey protein present in an amount of from about 0.25 wt % to about 1.75 wt % based on the weight of the the wound healing compostion.

5. The wound healing composition of claim 1, wherein the chitosan present in an amount of from about 0.25 wt % to about 1.75 wt % based on the weight of the the wound healing compostion.

6. A water-soluble, flowable powder, comprising the topical wound healing composition of claim 1.

7. A solution, comprising the topical wound healing composition of claim 1.

8. A topical dosage form selected from the group consisting of a cream, a lotion, an ointment, a foam, an aerosol, a powder, a solution, an emulsion, and a serum, comprising the wound healing compostion according to claim 1.

9. The topical wound healing composition of claim 1, wherein the topical wound healing composition does not comprise one or more of gluten, silica, an EU 26 fragrance allergen, a paraben, a formaldehyde releasing preservative, a growth factor or vitamin D.

10. A kit, comprising the topical wound healing composition of claim 1.

11. A method for treating compromised skin in a subject, comprising:
   topically administering to compromised skin of a subject in need thereof, a therapeutically effective amount of the topical wound healing composition according to claim 1.

12. The method of claim 11, wherein the topical wound healing composition is an aqueous solution.

13. The method of claim 12, wherein administering comprises applying a compress comprising the solution, to the compromised skin of the subject.

14. The method of claim 11, further comprising administering to the subject a topical soothing composition.

15. The method of claim 14, wherein the topical soothing composition comprises one or more of a glycosaminoglycan (GAG) stimulator, an anti-inflammatory, an antioxidant, and/or a DNA repair component.

16. The method according to claim 11, further comprising administering an epidermal/dermal repair composition.

17. The method of claim 16, wherein the epidermal/dermal repair composition comprises one or more of a skin protectant, a peptide a moisturizer, an anti-inflammatory, an antioxidant, a carrier, a solvent, a thickening agent, a humectant, an emulsifier, anti-bacterial agents, anti-microbial agents, anti-fungal agents, an emollient, an emulsifiying agent, a skin protectant active, a neutralizing agent, a preservative, a collagen Stimulator, a DNA protector, a moisturizing agent, soy phospholipids, a DNA repairing agent and a skin conditioning agent.

18. The method of claim 17, wherein the antioxidant is an antioxidant complex in the form of a 12-hour time release encapsulate.

19. A method for treating post-procedure skin in a subject following a skin procedure, comprising:
   dissolving a topical wound healing composition according to claim 1, in water to form a solution; and
   topically administering a therapeutically effective amount of the solution to post-procedure skin of a subject in need thereof.

20. The method of claim 19, wherein administering comprises applying a compress comprising the solution, to the post-procedure skin of the subject.

21. The method of claim 19, wherein the pH of the solution is from 3.5 to 5.3.

22. The method of claim 20, wherein the compress is a cloth or a gauze pad.

23. The method of claim 22, wherein the compress comprising the solution is applied with pressure to sections of the post-procedure skin starting at day 1 post-procedure, every two to three hours during the day.

* * * * *

UNITED STATES PATENT AND TRADEMARK OFFICE
CERTIFICATE OF CORRECTION

| | | |
|---|---|---|
| PATENT NO. | : 9,248,160 B1 | Page 1 of 1 |
| APPLICATION NO. | : 14/811264 | |
| DATED | : February 2, 2016 | |
| INVENTOR(S) | : Zein E. Obagi and Frederick W. Woodin, Jr. | |

It is certified that error appears in the above-identified patent and that said Letters Patent is hereby corrected as shown below:

In the claims,

Column 46, Claim 4, Line 7

Please delete "of the the wound"

and replace with -- of the wound --

Column 46, Claim 5, Line 11

Please delete "of the the wound"

and replace with -- of the wound --

Signed and Sealed this
Twelfth Day of April, 2016

Michelle K. Lee
*Director of the United States Patent and Trademark Office*